United States Patent
Swearingen

(10) Patent No.: US 8,618,339 B2
(45) Date of Patent: Dec. 31, 2013

(54) HIGH SELECTIVITY PROCESS TO MAKE DIHYDROFLUOROALKENES

(75) Inventor: Ekaterina N. Swearingen, Wilmington, DE (US)

(73) Assignee: E I du Pont de Nemours and Company, Wilmington, DE (US)

(*) Notice: Subject to any disclaimer, the term of this patent is extended or adjusted under 35 U.S.C. 154(b) by 959 days.

(21) Appl. No.: 12/110,890

(22) Filed: Apr. 28, 2008

(65) Prior Publication Data

US 2008/0269532 A1 Oct. 30, 2008

Related U.S. Application Data

(60) Provisional application No. 60/926,293, filed on Apr. 26, 2007.

(51) Int. Cl.
*C07C 17/00* (2006.01)
*C07C 21/00* (2006.01)

(52) U.S. Cl.
USPC .......................................................... 570/175

(58) Field of Classification Search
None
See application file for complete search history.

(56) References Cited

U.S. PATENT DOCUMENTS 5,063,194 A * 11/1991 Broecker et al. ............... 502/314
5,516,951 A * 5/1996 Aoyama ........................ 570/175
6,395,700 B1 * 5/2002 Yamada et al. ............... 510/412

FOREIGN PATENT DOCUMENTS

GB 810913 3/1959
JP 2004-292329 10/2004

OTHER PUBLICATIONS

Rylander, P. Hydrogenation Methods, 1985, 53-58.*
H. Burger et al : "Vibrational Spectra and Normal Coordinate Anaysis of CF3 Coumpounds", J. Mol Structure, vol. 84, 1982, pp. 49-68, XPOO2512757, p. 50, Paragraph 2.
A. L. Henne et al: "Perfluro-2-Butyne and Its Hydrogenation Products", J. Am. Chem. Cos., vol. 71, No. 1, 1949, pp. 298-300, XP00251260, *Hydrogenation of Hexafluorobutyne*, pp. 298, Right-Hand Column.
H. Lindlar et al: "Palladium Catalyst for Partial Reduction of Acetylenes", Organic Syntheses, vol. 5, 1973, p. 880-882, XP002512758, The Whole Document.
Hasek W R et al: The Chemistry of Sulfur Tetrafluoride. II. The Florination of Organi Carbonyl Society, Washing, DC.; US, US, vol. 82, Feb. 5, 1960, p. 543-551, XP00215300, ISSN: 0002-7863, The Whole Document.
Database Beilstein [Online], Beilstein Institue Fore Organic Chemistry, Frankfurt-Main, DE; XP002512761 Accession No. 993434, Abstract, & J.H. Atherton et al: J. Chem. Soc. Section C, 1967, pp. 1450-1454.
Database Beilstein [Online], Beilstein Institute for Organic Chemistry, Franfurt-Main, DE; XP002512762 Accession No. 1006978, Abstract, & R. Fields et al: J. Chem. Soc., 1964, pp. 1881-1889.
CRC Handbook of Chemistry and Physics, 61$^{st}$ Edition (2000-2001) (Book not Included).

* cited by examiner

Primary Examiner — Clinton Brooks

(57) ABSTRACT

Disclosed is a method for the synthesis of fluorinated alkenes comprising contacting a fluorinated alkyne of the formula $R^1 C{\equiv}C R^2$, wherein $R^1$ and $R^2$ are independently selected from $CF_3$, $C_2F_5$, $C_3F_7$, and $C_4F_9$, in a pressure vessel, with a Lindlar catalyst, with substantially one molar equivalent of hydrogen, to make the corresponding cis-alkene of formula $R^1 C{=}C R^2$ with high selectivity, wherein said hydrogen is added in portions over a period of time, so as to produce an initial pressure in the pressure in the vessel of no more than about 100 psi.

11 Claims, No Drawings

HIGH SELECTIVITY PROCESS TO MAKE DIHYDROFLUOROALKENES

BACKGROUND INFORMATION

1. Field of the Disclosure

This disclosure relates in general to the synthesis of hydrofluoroolefins.

2. Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well having low global warming potentials. Certain hydrofluoroolefins are believed to meet both goals. Thus there is a need for manufacturing processes that provide halogenated hydrocarbons and fluoroolefins that contain no chlorine that also have a low global warming potential.

SUMMARY

In one embodiment the process is a method for the synthesis of fluorinated alkenes comprising contacting a fluorinated alkyne of the formula $R^1$—C≡C—$R^2$, wherein $R^1$ and $R^2$ are independently selected from $CF_3$, $C_2F_5$, $C_3F_7$, and $C_4F_9$, in a pressure vessel, with a Lindlar catalyst, with substantially up to and including one molar equivalent of hydrogen, to make the corresponding cis or trans-alkene of formula $R^1$HC=CH$R^2$ with high selectivity, wherein said hydrogen is added in portions over a period of time, so as to produce an initial pressure in the vessel of no more than about 100 psi.

In another embodiment, the process is a method for the synthesis of fluorinated alkenes comprising: contacting a fluorinated alkyne of the formula $R_1$C≡C$R_2$, wherein $R_1$ and $R_2$ are independently selected from $CF_3$, $C_2F_5$, $C_3F_7$, and $C_4F_9$ in a pressure vessel, in a solvent, with a Lindlar catalyst, with substantially one molar equivalent of hydrogen, to make the corresponding cis-alkene of formula $R^1$HC=CH $R^2$ with high selectivity.

In yet another embodiment, the process is a method for synthesizing fluorinated alkenes in a continuous process, contacting a fluorinated alkyne of the formula $R^1$ C≡C $R^2$, wherein $R^1$ and $R^2$ are independently selected from $CF_3$, $C_2F_5$, $C_3F_7$, and $C_4F_9$, in a reaction zone, in the gas phase with substantially one equivalent or less of hydrogen in the presence of a Lindlar catalyst.

The foregoing general description and the following detailed description are exemplary and explanatory only and are not restrictive of the invention, as defined in the appended claims.

DETAILED DESCRIPTION

In one embodiment, the process is a method for the synthesis of fluorinated alkenes from the corresponding fluorinated alkynes in high selectivity by selective hydrogenation in the presence of particular catalysts.

Many aspects and embodiments have been described above and are merely exemplary and not limiting. After reading this specification, skilled artisans appreciate that other aspects and embodiments are possible without departing from the scope of the invention. Other features and benefits of any one or more of the embodiments will be apparent from the following detailed description, and from the claims.

Before addressing details of embodiments described below, some terms are defined or clarified.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, $81^{st}$ Edition (2000-2001).

As used herein, a reaction zone may be a reaction vessel fabricated from nickel, iron, titanium or their alloys, as described in U. S. Pat. No. 6,540,933, incorporated herein by reference. A reaction vessel of these materials (e.g., a metal tube) may also be used. When reference is made to alloys, it is meant a nickel alloy containing from about 1 to about 99.9 weight percent nickel, an iron alloy containing about 0.2 to about 99.8 weight percent iron, and a titanium alloy containing about 72 to about 99.8 weight percent titanium. Of note is the use of a tube such as above, packed with a Lindlar catalyst made of nickel or alloys of nickel such as those containing about 40 weight percent to about 80 weight percent nickel, e.g., Inconel™ 600 nickel alloy, Hastelloy™ C617 nickel alloy or Hastelloy™ C276 nickel alloy.

A Lindlar catalyst is a heterogeneous palladium catalyst on a calcium carbonate support, which has been deactivated or conditioned with a lead compound. The lead compound can be lead acetate, lead oxide, or any other suitable lead compound. In one embodiment, the catalyst is prepared by reduction of a palladium salt in the presence of a slurry of calcium carbonate, followed by the addition of the lead compound. In one embodiment, the palladium salt in palladium chloride. In another embodiment, the catalyst is deactivated or conditioned with quinoline. The amount of palladium on the support is typically 5% by weight but may be any catalytically effective amount.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

In one embodiment, fluorinated alkenes are synthesized by contacting fluorinated alkynes of the structure $R^1 C\equiv C R^2$, wherein $R^1$ and $R^2$ are independently selected from $CF_3$, $C_2F_5$, $C_3F_7$, and $C_4F_9$ with hydrogen in the presence of a selective catalyst. Representative fluorinated alkynes include alkynes selected from the group consisting of hexafluoro-2-butyne, octafluoro-2-pentyne, decafluoro-2-hexyne, decafluoro-3-hexyne, dodecafluoro-2-heptyne, dodecafluoro-3-heptyne, tetradecafluoro-3-octyne and tetradecafluoro-4-octyne.

Hexafluoro-2-butyne is readily available by dechlorination of 1,1,1,4,4,4-hexafluoro-2,3-dichloro-2-butene (CFC-1316mxx) with zinc. CFC-1316mxx is readily prepared from $CF_3CCl_3$ as disclosed in U.S. Pat. No. 5,919,994, which disclosure is herein incorporated by reference. Similarly, decafluoro-3-hexyne is readily prepared from $CF_3CF_2CCl=CClCF_2CF_3$ by dechlorination with zinc. $CF_3CF_2CCl=CClCF_2CF_3$ is similarly prepared from $CF_3CF_2CCl_3$. Similarly, decafluoro-2-hexyne is readily prepared from $CF_3CCl=CClCF_2CF_2CF_3$, which is readily prepared from CFC-1316mxx via reaction with tetrafluoroethylene in the presence of an aluminum chlorofluoride catalyst. Octafluoro-2-pentyne can be prepared from 1,1,1,2,2,3,4,5,5,5-decafluoropentane by dehydrofluroinating twice in the presence of base, or zeolites, as disclosed in Japanese patent 2004292329.

In one embodiment, the catalyst of the process is a Lindlar catalyst. In one embodiment, the amount of the catalyst used is from about 0.5% by weight to about 4% by weight of the amount of the fluorinated alkyne. In another embodiment, the amount of the catalyst used is from about 1% by weight to about 3% by weight of the amount of the fluorinated alkyne. In yet another embodiment, the amount of the catalyst used is from about 1% to about 2% by weight of the amount of the fluorinated alkyne.

In some embodiments, the reaction is conducted in a solvent. In one such embodiment, the solvent is an alcohol. Typical alcohol solvents include ethanol, i-propanol and n-propanol. In another embodiment, the solvent is a fluorocarbon or hydrofluorocarbon. Typical fluorocarbons or hydrofluorocarbons include 1,1,1,2,2,3,4,5,5,5-decafluoropentane and 1,1,2,2,3,3,4-heptafluorocyclopentane.

In one embodiment, the process is conducted in a batch-wise process.

In another embodiment, the process is conducted in a continuous process in the gas phase.

In one embodiment, reaction of the fluorinated alkynes with hydrogenation in the presence of the catalyst should be done with addition of hydrogen in portions, with increases in the pressure of the vessel of no more than about 100 psi with each addition. In another embodiment, the addition of hydrogen is controlled so that the pressure in the vessel increases no more than about 50 psi with each addition. In one embodiment, after enough hydrogen has been consumed in the hydrogenation reaction to convert at least 50% of the fluorinated alkyne to alkene, hydrogen can be added in larger increments for the remainder of the reaction. In another embodiment, after enough hydrogen has been consumed in the hydrogenation reaction to convert at least 60% of the fluorinated alkyne to alkene, hydrogen can be added in larger increments for the remainder of the reaction. In yet another embodiment, after enough hydrogen has been consumed in the hydrogenation reaction to convert at least 70% of the fluorinated alkyne to alkene, hydrogen can be added in larger increments for the remainder of the reaction. In one embodiment, the larger increments of hydrogen addition can be 300 psi. In another embodiment, the larger increments of hydrogen addition can be 400 psi.

In one embodiment, the amount of hydrogen added is about one molar equivalent per mole of fluorinated alkyne. In another embodiment, the amount of hydrogen added is from about 0.9 moles to about 1.3 moles, per mole of fluorinated alkyne. In yet another embodiment, the amount of hydrogen added is from about 0.95 moles to about 1.1 moles, per mole of fluorinated alkyne. In yet another embodiment, the amount of hydrogen added is from about 0.95 moles to about 1.03 moles, per mole of fluorinated alkyne.

In one embodiment, the hydrogenation is performed at ambient temperature. In another embodiment, the hydrogenation is performed at above ambient temperature. In yet another embodiment, the hydrogenation is performed at below ambient temperature. In yet another embodiment, the hydrogenation is performed at a temperature of below about 0° C.

In an embodiment of a continuous process, a mixture of fluorinated alkyne and hydrogen are passed through a reaction zone containing the catalyst. In one embodiment, the molar ratio of hydrogen to fluorinated alkyne is about 1:1. In another embodiment of a continuous process, the molar ratio of hydrogen to fluorinated alkyne is less than 1:1. In yet another embodiment, the molar ratio of hydrogen to fluorinated alkyne is about 0.67:1.0.

In one embodiment of a continuous process, the reaction zone is maintained at ambient temperature. In another embodiment of a continuous process, the reaction zone is maintained at a temperature of 30° C. In yet another embodiment of a continuous process, the reaction zone is maintained at a temperature of about 40° C.

In one embodiment of a continuous process, the flow rate of fluorinated alkyne and hydrogen is maintained so as to provide a residence time in the reaction zone of about 30 seconds. In another embodiment of a continuous process, the flow rate of fluorinated alkyne and hydrogen is maintained so as to provide a residence time in the reaction zone of about 15 seconds. In yet another embodiment of a continuous process, the flow rate of fluorinated alkyne and hydrogen is maintained so as to provide a residence time in the reaction zone of about 7 seconds.

It will be understood, that contact time in the reaction zone is reduced by increasing the flow rate of fluorinated alkyne and hydrogen into the reaction zone. As the flow rate is increased this will increase the amount of fluorinated alkyne being hydrogenated per unit time. Since the hydrogenation is exothermic, depending on the length and diameter of the reaction zone, and its ability to dissipate heat, at higher flow rates it may be desirable to provide a source of external cooling to the reaction zone to maintain a desired temperature.

In one embodiment of a continuous process, the amount of palladium on the support in the Lindlar catalyst is 5% by weight. In another embodiment, the amount of palladium on the support in the Lindlar catalyst is greater than 5% by weight. In yet another embodiment, the amount of palladium on the support can be from about 5% by weight to about 1% by weight.

In one embodiment, upon completion of a batch-wise or continuous hydrogenation process, the cis-dihydrofluoroalkene can be recovered through any conventional process, including for example, fractional distillation. In another embodiment, upon completion of a batch-wise or continuous hydrogenation process, the cis-dihydrorofluoroalkene is of sufficient purity to not require further purification steps.

EXAMPLES

The concepts described herein will be further described in the following examples, which do not limit the scope of the invention described in the claims.

Example 1

Example 1 demonstrates the selective hydrogenation of hexafluoro-2-butyne.

5 g of Lindlar (5% Pd on CaCO3 poisoned with lead) catalyst was charged in 1.3 L rocker bomb. 480 g (2.96 mole) of hexafluoro-2-butyne was charged in the rocker. The reactor was cooled down (−78° C.) and evacuated. After the bomb was wormed up to room temperature, $H_2$ was added slowly, by increments which did not exceed $\Delta p=50$ psi. A total of 3 moles $H_2$ were added to the reactor. A gas chromatographic analysis of the crude product indicated the mixture consisted of $CF_3C\!\!\equiv\!\!CCF_3$ (0.236%), trans-isomer of $CF_3CH\!\!=\!\!CHCF_3$ (0.444%), saturated $CF_3CH_2CH_2CF_3$ (1.9%) $CF_2\!\!=\!\!CHCl$, impurity from starting butyne, (0.628%), cis-isomer of $CF_3CH\!\!=\!\!CHCF_3$ (96.748%). Distillation afforded 287 g (59% yield) of 100% pure cis-$CF_3CH\!\!=\!\!CHCF_3$ (boiling point 33.3° C.). MS: 164 [MI], 145 [M-19], 95 [$CF_3CH\!\!=\!\!CH$], 69 [$CF_3$]. NMR $H^1$: 6.12 ppm (multiplet), $F^{19}$: −60.9 ppm (triplet J=0.86 Hz)

Example 2

Example 2 demonstrates the hydrogenation of hexafluoro-2-butyne with 2% catalyst by weight.

Into a 1.3 l Hastelloy reactor 10 g of Lindlar catalyst was loaded. Then, hexafluoro-2-butyne 500 g (3.08 mole) was added to the reactor. Hydrogen was added by small increments of 50-100 psi. A total of 1100 psi of hydrogen was added in total. (3.08 mole) Hydrogen was consumed at the rate of 150 psi/hr average during 6.5 hrs. Analysis of the product by gas chromatography indicated that 93.7% of hexafluorobutyne was converted into cis-$CF_3CH\!\!=\!\!CHCF_3$, with 4.8% of saturated $CF_3CH_2CH_2CF_3$.

Example 3

Example 3 demonstrates the hydrogenation of octafluoro-2-pentyne with 1% catalyst by weight.

Into a 1.3l Hastelloy reactor 10 g of Lindlar catalyst is loaded. Then, octafluoro-2-pentyne 650 g (3.06 mole) is added to the reactor. Hydrogen is then added slowly, by increments which do not exceed $\Delta p=50$ psi. A total of 3 moles $H_2$ is added to the reactor. Analysis of the product by gas chromatography indicated that 96.7% of octafluoro-2-pentyne is converted into cis-$CF_3CH\!\!=\!\!CHCF_2CF_3$, with 1.8% of saturated $CF_3CH_2CH_2CF_2CF_3$.

Example 4

Example 4 demonstrates the hydrogenation of hexafluoro-2-butyne with 1% catalyst by weight.

Into a 1.3l Hastelloy reactor 5 g of Lindlar catalyst was loaded. Then, hexafluoro-2-butyne 500 g (3.08 mole) was added to the reactor. Hydrogen was added by small increments of 30-50 psi. 1414 psi was added total (4.0 moles hydrogen). Hydrogen was consumed at the rate of 50 psi/hr average during 28 hrs. Analysis of the resulting product mixture indicated 80.7% cis-$CF_3CH\!\!=\!\!CHCF_3$, and 19.3% saturated $CF_3CH_2CH_2CF_3$ Example 5

Example 5 demonstrates the hydrogenation of decafluoro-3-hexyne.

Into a 1.3l Hastelloy reactor 8 g of Lindlar catalyst is loaded. Then, decafluoro-3-hexyne 800 g (3.05 mole) is added to the reactor. Hydrogen is then added slowly, by increments which do not exceed $\Delta p=50$ psi. A total of 3 moles $H_2$ is added to the reactor. Analysis of the product by gas chromatography indicated that 96.7% of decafluoro-3-hexyne is converted into cis-$CF_3CF_2CH\!\!=\!\!CHCF_2CF_3$, with 1.8% of saturated $CF_3CF_2CH_2CH_2CF_2CF_3$.

Example 6

Example 6 demonstrates the hydrogenation of hexafluoro-2-butyne in a continuous process to produce a mixture of cis- and trans-1,1,1,4,4,4-hexafluoro-2-butene.

A Hastelloy tube reactor 10" long with a 5" O.D. (outside diameter) and 0.35" wall thickness was filled with 10 g of Lindlar catalyst. The catalyst was conditioned at 70° C. with a flow of hydrogen for 24 hours. Then a flow of a 1:1 mole ratio of hexafluoro-2-butyne and hydrogen was passed through the reactor at 30° C. at a flow rate sufficient to provide a 30 second contact time. The product mixture was collected in a cold trap after exiting the reactor and analyzed by gas chromatography. The product mixture was found to contain $CF_3CH\!\!=\!\!CHCF_3$ (cis) (72%), $CF_3CH\!\!=\!\!CHCF_3$ (trans) (8.8%), $CF_3CH_2CH_2CF_3$ (7.8%) and $CF_3C\!\!\equiv\!\!CCF_3$ (3.3%).

Example 7

Example 7 demonstrates the hydrogenation of hexafluoro-2-butyne in a continuous process with a 15 second contact time.

The procedure of example 6 was followed, with the exception that the flow rate was adjusted to provide a contact time of 15 seconds. The reaction was slightly exothermic, with the reactor warming to 35-36° C. Analysis of the product mixture indicated $CF_3CH\!\!=\!\!CHCF_3$ (cis) (72%), $CF_3CH\!\!=\!\!CHCF_3$ (trans) (9.3%), $CF_3CH_2CH_2CF_3$ (11.3%) and $CF_3C\!\!\equiv\!\!CCF_3$ (3.9%).

Example 8

Example 8 demonstrates the hydrogenation of hexafluoro-2-butyne in a continuous process with a hydrogen:alkyne mole ratio of 0.67:1.

The procedure of example 6 was followed, with the exception that the mole ratio of hydrogen:hexafluoro-2-butyne fed to the reactor was 0.67:1.0. Analysis of the product mixture indicated $CF_3CH\!\!=\!\!CHCF_3$ (cis) (65.3%), $CF_3CH\!\!=\!\!CHCF_3$ (trans) (4.4%), $CF_3CH_2CH_2CF_3$ (3.4%) and $CF_3C\!\!\equiv\!\!CCF_3$ (23.5%).

Example 9

Example 9 demonstrates the hydrogenation of hexafluoro-2-butyne in a continuous process with a 7 second contact time.

The procedure of example 6 was followed, with the exception that the flow rate was adjusted to provide a contact time of 7 seconds. The reaction was slightly exothermic, with the reactor warming to 42° C. Analysis of the product mixture indicated $CF_3CH=CHCF_3$ (cis) (72.5%), $CF_3CH=CHCF_3$ (trans) (8.7%), $CF_3CH_2CH_2CF_3$ (8.6%) and $CF_3C\equiv CCF_3$ (6.9%).

Comparative Example 1

Into a 400 ml Hastelloy shaker tube was loaded with 2 g of Lindlar catalyst, 30 g of hexafluoro-2-butyne. The shaker was pressurized up to 300 psi with $H_2$. The pressure suddenly rose to 4000 psi, and the temperature of the reactor contents went up to 70° C. Black powder was recovered as a product.

Comparative Example 2

Into a 1.31 Hastelloy reactor 10 g of Lindlar catalyst was loaded. Then, hexafluoro-2-butyne 500 g (3.08 mole) was added to the reactor. Hydrogen was added by small increments of 30-50 psi. 2385 psi was added total. At the rate 40 psi/hr average. Hydrogen was consumed at the rate of 35 psi/hr average during 60 hrs. As a result 89% of hexafluoro-2-butyne was converted into saturated $CF_3CH_2CH_2CF_3$, 7.7% of unsaturated cis-$CF_3CH=CHCF_3$ was detected in the mixture of products.

Comparative Example 3

Into Hastelloy 210 ml shaker tube 1 g of Raney Ni was placed. After the reactor was cool 25 g (0.154 mole) of hexafluoro-2-butyne was added. The reactor was pressurized to 150 psi (approx., 0.09 mole) with $H_2$ at ambient temperature. The reactor was then heated to 50° C. The pressure went up to 299 psi at 52° C. and the following one hour dropped only 14 psi. After increasing temperature to 90° C., the pressure dropped to 214 psi and didn't change during 3 additional hours. After carefully venting the remaining pressure, 20 g of crude product mixture was recovered. The mixture contained 86% of starting hexafluoro-2-butyne, 8.375% of saturated $CF_3CH_2CH_2CF_3$ and 5.6% of cis-$CF_3CH=CHCF_3$.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for hydrogenation, comprising: contacting a fluorinated alkyne of the formula $R^1 C\equiv C R^2$, wherein $R^1$ and $R^2$ are independently selected from $CF_3$, $C_2F_5$, $C_3F_7$, and $C_4F_9$, with substantially one equivalent or less of hydrogen in a reaction zone, in the gas phase in the presence of a Lindlar catalyst to make a fluorinated alkene of formula $R^1 CH=CH R^2$.

2. The process of claim 1 wherein the fluorinated alkyne is selected from the group consisting of hexafluoro-2-butyne, octafluoro-2-pentyne, decafluoro-2-hexyne, decafluoro-3-hexyne, dodecafluoro-2-heptyne, dodecafluoro-3-heptyne, tetradecafluoro-3-octyne and tetradecafluoro-4-octyne.

3. The process of claim 1 wherein the ratio of hydrogen to fluorinated alkyne is from about 0.67:1 to about 1:1.

4. The process of claim 1 wherein the weight percent of palladium catalyst on calcium carbonate support is from about 1% by weight to about 10% by weight.

5. The process of claim 1 wherein the weight percent of palladium catalyst on calcium carbonate support is from about 1% by weight to about 5% by weight.

6. The process of claim 1 wherein the fluorinated alkyne fed to the reaction zone further comprises an inert carrier gas.

7. The process of claim 6 wherein the inert carrier gas is selected from the group consisting of nitrogen, helium or argon.

8. The process of claim 1, further comprising, recovering a product mixture comprising the said cis- isomer of said fluorinated alkene of formula $R^1 CH=CH R^2$ by factional distillation.

9. The process of claim 1, wherein the said fluorinated alkene product of formula $R^1 CH=CH R^2$ comprises both the cis- and trans- isomers.

10. The process of claim 9, wherein the trans- isomer of the fluorinated alkene product is at least 5% by weight of the fluorinated alkene product.

11. The process of claim 9, wherein the trans- isomer of the fluorinated alkene product is at least 10% by weight of the fluorinated alkene product.

* * * * *